United States Patent [19]

Bodicky

[11] Patent Number: 4,563,171
[45] Date of Patent: Jan. 7, 1986

[54] METHOD FOR DISPLACING FLUID IN TUBING

[75] Inventor: Raymond O. Bodicky, St. Louis, Mo.

[73] Assignee: Sherwood Medical Company, St. Louis, Mo.

[21] Appl. No.: 692,876

[22] Filed: Jan. 18, 1985

Related U.S. Application Data

[63] Continuation of Ser. No. 135,062, Mar. 28, 1980, abandoned.

[51] Int. Cl.⁴ ............................................. A61M 27/00
[52] U.S. Cl. .......................................... 604/51; 604/73
[58] Field of Search ..................... 604/7, 8, 9, 10, 19,
   604/21, 27, 28, 30, 31, 34, 36, 48, 49, 51, 56, 73,
   93, 118, 128, 131, 150, 151, 152, 153, 181, 185,
   192; 222/95, 407; 417/478; 128/281, 321, 350

[56] References Cited

U.S. PATENT DOCUMENTS

| | | | |
|---|---|---|---|
| 2,542,505 | 2/1951 | Gascoigne | 128/281 |
| 2,737,151 | 3/1956 | Gaertner | 119/14.22 |
| 3,194,452 | 7/1965 | Sanderford | 222/407 |
| 3,248,012 | 4/1966 | Adams | 222/95 |
| 3,648,701 | 3/1972 | Botts | 128/321 |
| 3,780,740 | 12/1973 | Rhea | 128/350 R |
| 4,164,223 | 8/1979 | Munib | 128/321 |
| 4,248,224 | 2/1981 | Jones | 128/350 R |
| 4,268,226 | 5/1981 | Morris | 417/478 |

FOREIGN PATENT DOCUMENTS

| | | | |
|---|---|---|---|
| 278763 | 2/1952 | Switzerland | |
| 1301393 | 12/1972 | United Kingdom | 128/207.14 |

*Primary Examiner*—Edward A. Miller
*Assistant Examiner*—T. J. Wallen
*Attorney, Agent, or Firm*—Stanley N. Garber; William R. O'Meara

[57] ABSTRACT

A method and apparatus for conveying fluids includes tubing and a tube clearing sleeve surrounding the tubing. The sleeve has a slick inner surface with a coefficient of friction less than that of the outer surface of the tubing. The sleeve is compressed between the fingers to compress the tubing and the compressed sleeve is advanced along the tubing to displace contents in the tubing.

13 Claims, 4 Drawing Figures

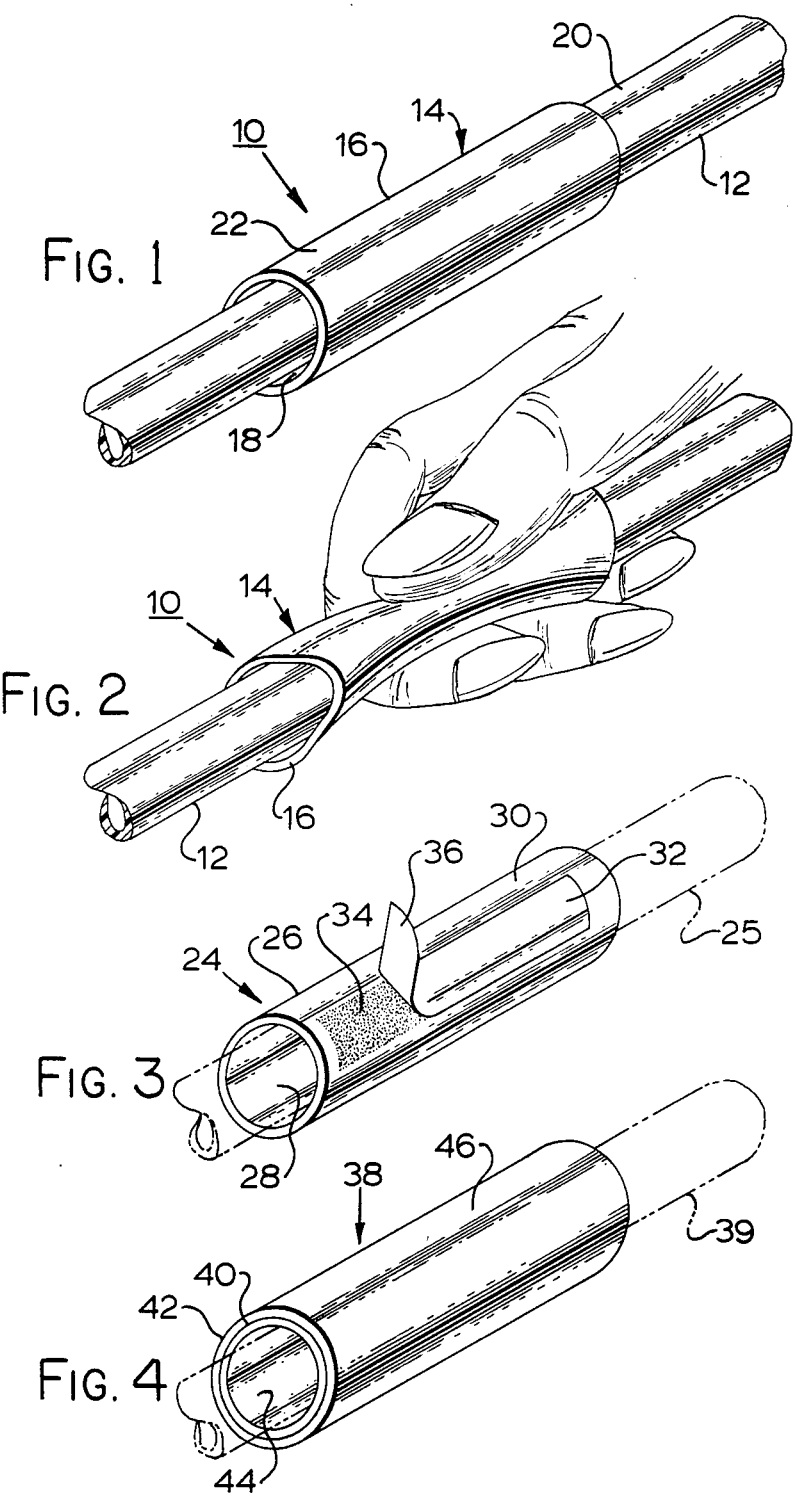

METHOD FOR DISPLACING FLUID IN TUBING

This application is a continuation, of application Ser. No. 135,062, filed Mar. 28, 1980, and now abandoned.

DESCRIPTION

1. Technical Field

This invention relates to the conveying of fluids through tubing and more particularly to manually operated fluid displacing means for fluid conveying tubing.

2. Background Art

Tubing is used, for example, extensively in hospitals to convey fluids for various purposes including introducing fluids into the body and withdrawing fluids from the body. In body fluid drainage systems, for example, in chest drainage apparatus, an elastomeric tube is connected at one end to a chest drainage catheter connected to the plural cavity of the patient, and the opposite end of the tube is connected to a fluid drainage collection bottle or chamber. Such drainage apparatus may collect drainage either by the effects of gravity alone or by a vacuum assist.

In such chest drainage systems, fibrin or a blood clot may occlude the tube or restrict the fluid discharge rate of flow. It has been common practice for the attendant to displace or clear the contents of the tube and remove the obstruction by hand. Because the tubing is generally made of a material which produces an outer surface with a relatively high coefficient of friction, such as polyvinyl chloride, latex, polyurethane or silicone, the fingers are generally first lubricated by applying an oil or grease to them. Then, while squeezing and compressing the tube between the fingers, the fingers are advanced longitudinally along the tube to move fluid and other matter through the tube thereby removing the obstruction or increasing the fluid flow rate. Clearing solids, semi-solids, or liquids from resilient, flexible tubing in various other fluid systems is often accomplished in a similar manner. If a lubricant is not employed, the friction between the fingers and tubing would cause chafing of the skin. Even when a lubricant is used, some chafing of the sking occurs and the tubing may not be cleared as well as it should be. Also, the use of lubricants is time consuming since it requires the application, as well as, removal of lubricant from the hand.

In order to avoid the above mentioned problems associated with the above manner of stripping or clearing the contents of tubing, various hand tools having rollers have been proposed. The tubing is clamped between the rollers and then the rollers are moved along the tubing to move the tubing contents longitudinally. Devices of this general type are disclosed in U.S. Pat. Nos. 3,194,452, 3,648,701, and 4,164,223, and in Switzerland Patentschrift No. 278,763, Feb. 16, 1952. These roller devices require a number of parts that must be assembled including pivotally connected arms carrying opposed tube rollers etc. These devices are not only relatively expensive but are relatively large and generally cumbersome in use.

BRIEF SUMMARY OF THE INVENTION

One or more of the above mentioned problems are overcome in accordance with one aspect of the present invention by providing a manually collapsible fluid displacing means such as a sleeve, over tubing adapted to convey a fluid. The fluid displacing means has an inner surface with a relatively low coefficient of friction compared to that of the outer surface of the tubing so that it is slideable along the tubing. The sleeve can be manually clamped against the tubing to compress the tubing and then be readily slid along the tubing to displace contents of the tubing. In accordance with another aspect of the invention, the outer surface of the fluid displacing means has a higher coefficient of friction than the inner surface thereof to increase the friction between the outer surface of the sleeve and the hand of the person using the sleeve member.

BRIEF DESCRIPTION OF THE DRAWING

FIG. 1 is a perspective view of an apparatus for conveying fluid and having a hand fluid displacing device in accordance with a preferred embodiment of the invention;

FIG. 2 is a perspective view of the fluid conveying apparatus of FIG. 1 illustrating the method of manually displacing the contents of the tubing of FIG. 1;

FIG. 3 is a perspective view of a tube contents displacing member in accordance with a modified embodiment; and FIG. 4 is a perspective view of a tube contents displacing member in accordance with another modified embodiment of the invention.

DETAILED DESCRIPTION OF THE DRAWING

Refering now to the drawing and particularly to FIG. 1, there is illustrated medical tubing apparatus, indicated generally at 10, including tubing 12 and a fluid displacing or type clearing member 14 on the tubing 12. Apparatus 10 is especially well suited for use in a chest drainage system. Tubing 12 may have one end connected to a catheter (not shown) that is connected to the plural cavity of the patient. The opposite end of tubing 12 may be connected to a fluid drainage collection bottle or chamber (not shown). Drainage flow from the patient to the collection chamber may be effected by gravity or assisted by a suitable vacuum applied to the collection chamber.

The tubing 12 may be of any suitable rubber or plastic, for example, it may formed or extruded from a material which includes latex, polyvinyl chloride, silicone, polyurethane or the like. The tubing 12 is an elastomeric tube which is flexible, resilient, and elastic, and which is collapsible or compressible, and returns to its original shape after deformation. Preferably, the opposed walls can be totally collapsed to effect a closure across the inside of the tube by manually pinching the tubing. Latex and polyvinyl chloride tubing is often used in chest drainage systems. All of the above material can be extruded to produce tubes, such as tubing 12. Such tubing has an outer surface which has a relatively high coefficient of friction with respect to the human skin such as on the fingers of the hand.

The fluid displacing or tube clearing member 14 is shown including a sleeve 16 surrounding the tubing 12 and having an inner diameter slightly greater than the outer diameter of tubing 12. For example, the outer diameter of tubing 12 may be 0.65 inch and the inner diameter of sleeve 16 0.75 inch. Sleeve 16 is formed of a material that produces an inner surface 18 which has a relatively low coefficient of friction with respect to the outer surface 20 of the tubing 12 so that even when pressed together with some force, the sleeve 16 is readily slideable relative to the tubing 12. The sleeve 16 may be made from a plastic and is preferably made from Teflon, that is either tetra fluoroethylene (TFE) or fluoroethylenepropylene(FEP). TFE is generally more economical than FEP. Either may be extruded to produce tubing from which sleeves, such as sleeve 16 can be cut. Such sleeves have a slick or low friction inner surface 18, as well as a slick or low friction outer surface 22. The sleeve may be relatively thin, for example, a wall thickness of 0.015 inch will generally be suitable. Since sleeve 16 is to be grasped by the hand or fingers of the person or attendant operating the fluid drainage system, as will be discussed hereafter, a suitable longitudinal length for the sleeve is about three inches.

In use, if a blockage or partial occlusion of tube 12 occurs due, for example, to chest drainage matter clogging the tube, or if it is otherwise desired to increase the fluid flow rate of the tube contents, the operator hand grasps sleeve 16, such as between the fingers as shown in FIG. 2. With the fingers engaging the outer surface 22, the sleeve 16 is pinched to compress or collapse the sleeve and tube to either occlude or partially occlude the tube 12. While maintaining the tube compressed, the fingers and sleeve 16 are advanced longitudinally along the tube 12 thereby causing the contents of the tube to advance and to generally displace tube contents into the collection chamber. This can break up a blockage and open the tube lumen for the free flow of fluid.

Dislodging drainage matter may also be accomplished by first pinching the tube 12 with one hand to occlude it, and simultaneously compressing the sleeve and tube, as indicated above, and advancing the compressed sleeve in a direction away from the occlusion. This creates a reduced or negative pressure in the tube 12 between the pinched zone and the compressed sleeve zone. When the one hand releases the pinched area of the tube, the pressure differential created on opposite sides of the occluding matter can cause such matter to be released or dislodged.

Because the inner surface 18 of the fluid displacing sleeve 16 has a low coefficient of friction compared to the outer surface 20 of tubing 12, the sleeve readily slides along the tubing 12 while it and the tubing 12 are compressed by the fingers. Since the fingers and sleeve move together there is no chafing or wear of the skin of the operator during the relative movement of the sleeve and tube. Relatively high pinching pressures can be applied through the sleeve 16 by the fingers to collapse tubing 12 and yet there is no chafing of the fingers.

As shown in FIG. 3, fluid conveying apparatus is shown including a cylindrical fluid displacing or tube clearing member 24 of modified construction surrounding fluid conveying tubing shown in phantom at 25. The tube clearing member 24 includes a collapsible cylindrical sleeve 26 such as a thin sleeve or tube of plastic having a lower coefficient of friction than that of the tubing 25. Preferably, the sleeve 26 is formed of Teflon, either TFE or FEP, so that the inner surface 28 of the sleeve will be relatively slick and readily slideable over tubing 25. The outer surface 30 of the sleeve in such case will also be relatively slick.

In some cases, it is desirable to increase the friction between the fingers and the outer surface of the sleeve 26 so that there is little or substantially no relative movement between the fingers and sleeve during use of the tube clearing device. This is especially important where the attendant is subject to having water or other materials on the hands which might cause the fingers to slip off of the sleeve during use. A friction tape 32 is illustrated in FIG. 3 as being applied longitudinally along the outer surface 30 of the sleeve. The tape 32 may be of the conventional type which has a layer 34 coated on both sides with a non-drying adhesive, and a peel-back paper cover layer 36. The tape 32 may be applied and the cover layer 36 removed as indicated in FIG. 3 to expose the outer adhesive of layer 34. A plurality of such tapes may be applied where desired. The adhesive surface prevents or reduces relative movement between the fingers and the sleeve during use.

In FIG. 4 a fluid conveying system is shown including a modified tube clearing device 38 surrounding resilient, compressible tubing 39. The clearing device includes an inner cylindrical sleeve 40 of material having a low coefficient of friction, preferably of TFE or FEP, and a concentric outer cylindrical sleeve 42 of a material having a relatively higher coefficient of friction than sleeve 40. The inner surface 44 of sleeve 40 has a lower coefficient of friction than tubing 39 so that it readily slides along the tubing 39 while compressing the tubing. The outer surface 46 of outer sleeve 42 provides a higher coefficient of friction between the fingers of the operator and the clearing device 38 to prevent or reduce relative movement during use or prevent the fingers from slipping off of the device.

The outer sleeve 42 may be formed, for example, of any of the previously mentioned materials useful in making the fluid conveying tubing. The outer sleeve 42 may be secured to the inner Teflon layer by passing the inner sleeve through an extruder dieand extruding a thermoplastic material, for example, polyvinyl chloride, onto the outer surface of the inner sleeve. Another method is to form the outer sleeve 42 of a highly elastic material such as a thin latex sleeve and stretch it onto the inner sleeve 40. In the latter case the resilience of the latex holds it in place.

The tube clearing devices described herein are simple in construction, light weight, economical and need no special storage area. Since they can be readily packaged with and disposed on the drainage tubing, the tube clearing device is immediately available for use in clearing or reducing obstructions or displacing contents of the tubing. It is, of course, especially important in emergency situations to have a tube clearing device at hand.

Because of the relatively low cost of the disclosed tube clearing devices, they can be employed extensively in hospitals, and can be discarded with the disposable tubing as a disposable item.

While the tube clearing devices and sleeves illustrated in the drawings are circumferentially continuous and are shown circular in cross-section when in an uncompressed state, other shapes may be used.

When one material or surface is stated herein to have a lower or higher coefficient of friction than a second surface or material, it is intended that the coefficient of friction of the two members or surfaces are compared when they are subjected to like pressures and moving forces when engaged against a standard surface (for example a glass surface).

As various changes can be made in the above construction and method without departing from the scope of the invention, it is intended that all matter contained in the above description and shown in the accompanying drawing shall be interpreted as illustrative and not in a limiting sense.

I claim:

1. A method of draining body fluid from a body cavity through a medical tube a fluid collection container and displacing obstructions in the lumen of the tube when such occurs to assist the flow of body drainage fluid to the container, comprising the steps of providing a manually collapsible, resilient tube having a normally uncollapsed lumen and an outer surface with a relatively high coefficient of friction, and a manually collapsible flexible sleeve of predetermined length having an inside diameter somewhat larger than the outside diameter of the tube and disposed on the tube in surrounding relation therewith with the inner surface of the sleeve engageable with the outer surface of the tube, the sleeve having an inner surface with a coefficient of friction substantially less than that of the outer surface of the tube, connecting the tube in fluid communication between a body cavity and a fluid collection container, grasping the outer surface of the sleeve with the hand and collapsing the sleeve and the tube by manually applying compressive forces thereto to collapse the tube lumen at the sleeve, while applying compressive forces and holding the sleeve and the tube lumen collapsed, advancing the sleeve longitudinally along the tube with the inner surface of the sleeve in sliding contact with the outer surface of the tube for displacing an obstruction in the tube lumen, and removing the manually applied compressive forces to release the sleeve and tube and allow the resiliency of the tube to return the tube lumen to an uncollapsed condition at the sleeve for allowing drainage fluid to flow through the lumen from the body cavity to the fluid container.

2. The method of claim 1 including the step of pinching the tube with one hand and advancing the sleeve longitudinally along the tube with the other hand.

3. The method of claim 1 repeating, as desired, said step of advancing the sleeve longitudinally along the tube and said step of removing the compressive forces upon the occurrence of another obstruction in the tube lumen.

4. The method of claim 1 wherein said step of advancing the sleeve longitudinally along the tube includes advancing the sleeve in a direction to displace fluid in the tube lumen toward the fluid collection container.

5. The method of claim 1 wherein the tube is of elastomeric material.

6. The method of claim 1 wherein the sleeve comprises a layer of a material which includes tetra fluoroethylene, and wherein said material is in sliding contact with the outer surface of the tube during said step of advancing the sleeve.

7. The method of claim 6 wherein the material of the tube includes latex.

8. The method of claim 1 wherein the sleeve comprises a layer of a material which includes fluoroethylenepropylene and wherein said material is in sliding contact with the outer surface of the tube during said step of advancing the sleeve.

9. The method of claim 1 wherein the tube is made of a material which includes a material selected from the group consisting of latex, polyurethane, silicone, and polyvinyl chloride.

10. The method of claim 1 wherein the sleeve has an outer surface with a coefficient of friction greater than that of the inner surface thereof.

11. The method of claim 1 wherein the sleeve has an outer surface area with a coefficient of friction greater than that of the inner surface of the sleeve, and a removable cover layer over said outer surface area.

12. The method of claim 1 wherein the sleeve is generally circular in cross-section.

13. The method of claim 1 wherein the inner surface of the sleeve is the inner surface of an inner layer of material of the sleeve and the sleeve also includes an outer layer of material connected to and concentric with the inner layer, the outer surface of the outer layer has a higher coefficient of friction than that of said inner surface of the inner layer.

* * * * *